United States Patent [19]
Karami

[11] 3,965,906
[45] June 29, 1976

[54] ABSORBENT ARTICLE WITH PATTERN AND METHOD
[75] Inventor: Hamzeh Karami, Crystal Lake, Ill.
[73] Assignee: Colgate-Palmolive Company, New York, N.Y.
[22] Filed: Feb. 24, 1975
[21] Appl. No.: 552,464

[52] U.S. Cl............................. 128/287; 156/201; 128/156; 128/290 R
[51] Int. Cl.² .................. A41B 13/02; A61F 13/18
[58] Field of Search........ 128/156, 284, 287, 290 R, 128/296; 428/198, 195; 156/201

[56] References Cited
UNITED STATES PATENTS

| | | |
|---|---|---|
| 3,221,738 | 12/1965 | Ekberg et al. ..................... 128/287 |
| 3,814,101 | 6/1974 | Kozak ................................. 128/287 |
| 3,868,287 | 2/1975 | Lewyckyj ........................... 156/201 |
| 3,875,942 | 4/1975 | Roberts............................... 128/287 |
| 3,881,489 | 5/1975 | Hartwell ............................. 128/287 |
| 3,886,941 | 6/1975 | Duane................................. 128/287 |

*Primary Examiner*—Aldrich F. Medbery
*Attorney, Agent, or Firm*—Powell L. Sprunger

[57] ABSTRACT

An absorbent article comprising an absorbent pad having a front surface, and sheet means, including a film of thermoplastic material, covering at least a portion of the front surface of the pad. A pattern is fused into the film to define a discontinuous front surface of the article.

15 Claims, 12 Drawing Figures

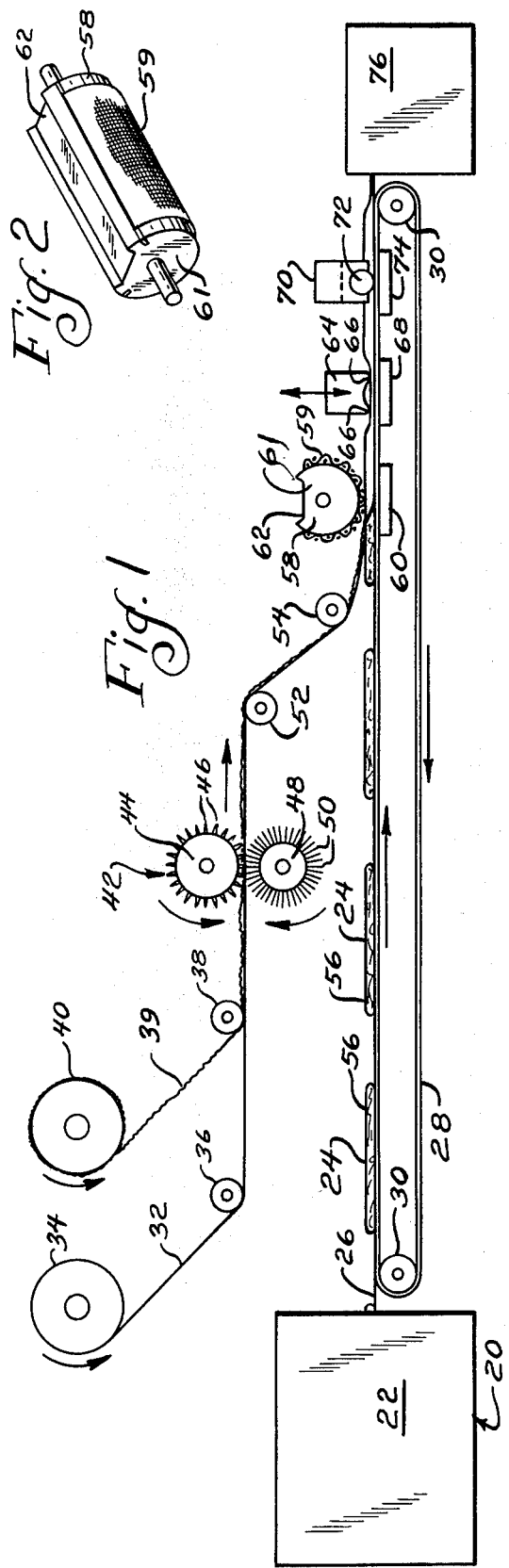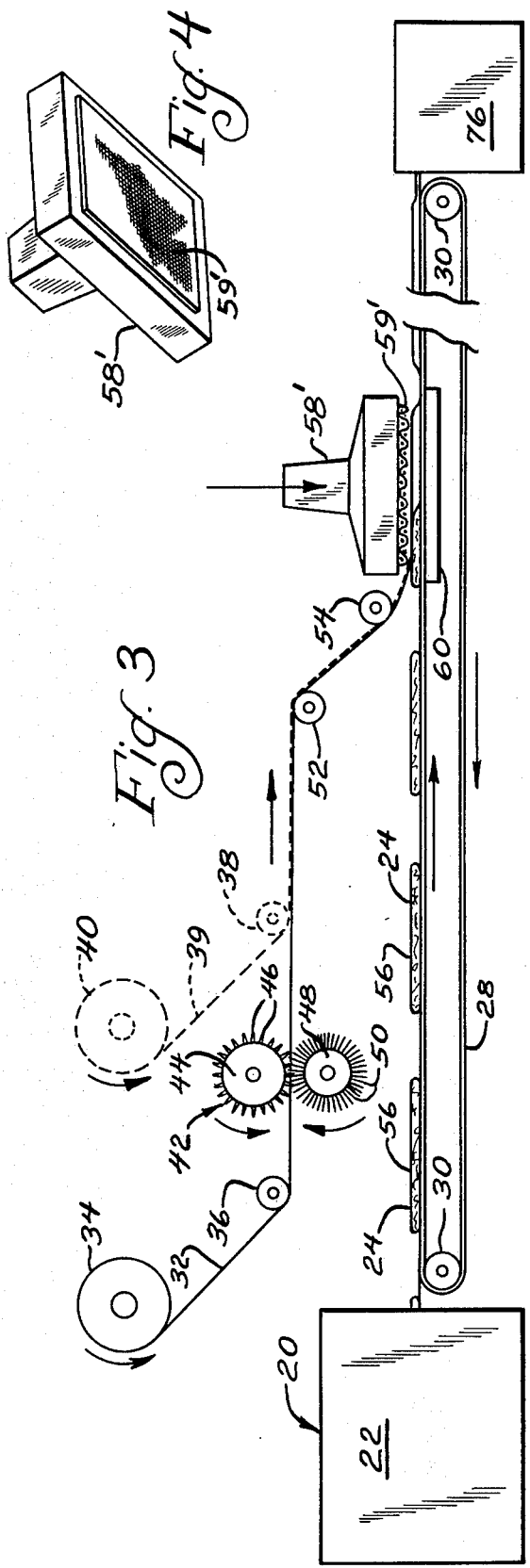

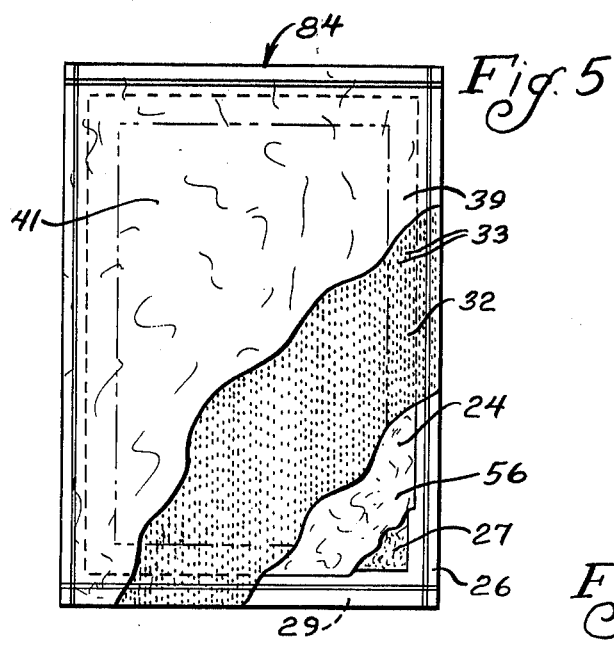
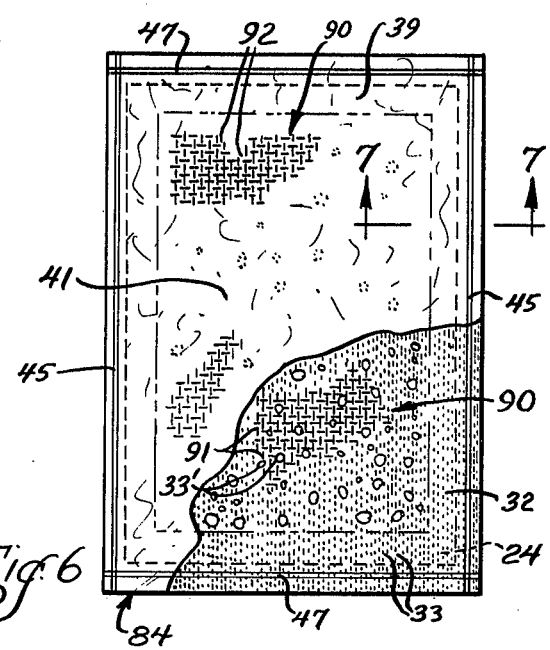
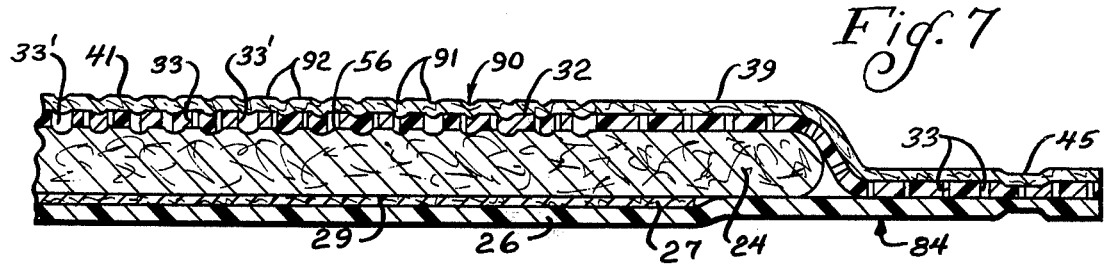
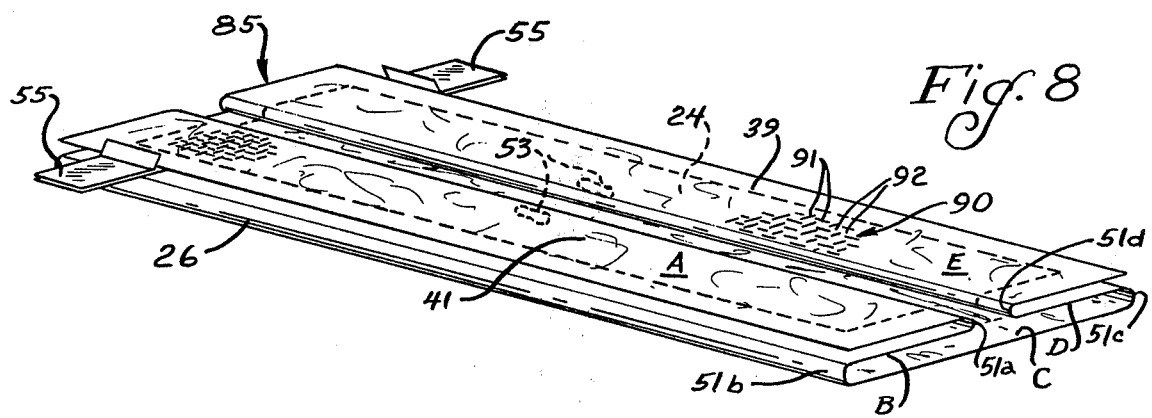

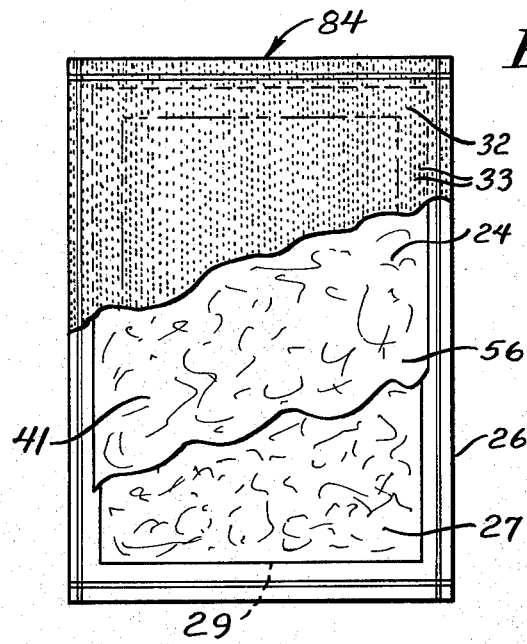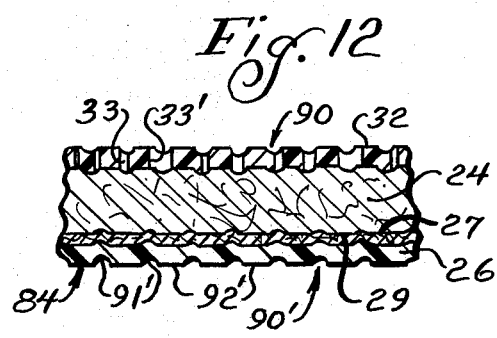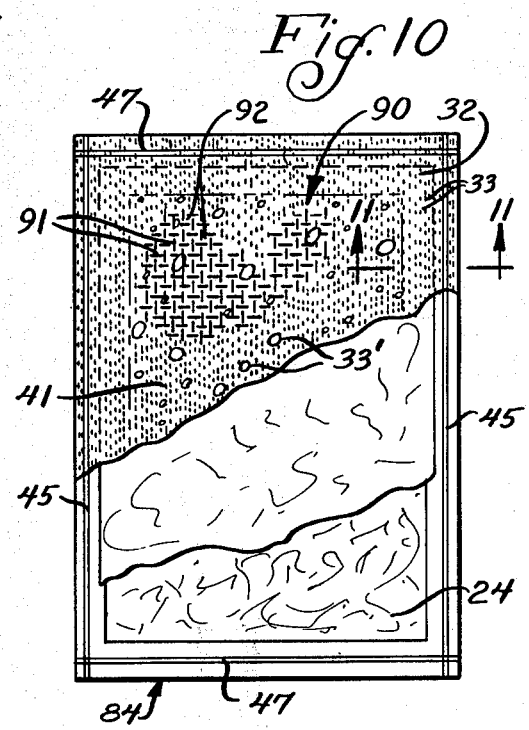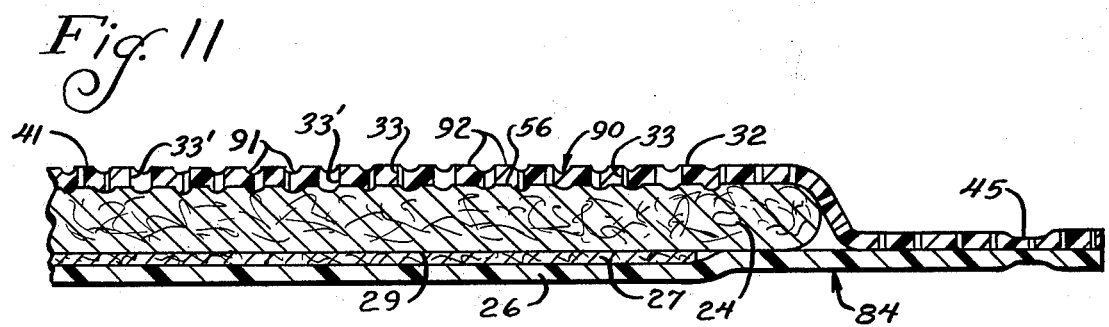

ABSORBENT ARTICLE WITH PATTERN AND METHOD

BACKGROUND OF THE INVENTION

The present invention relates to absorbent articles.

A various assortment of absorbent articles of the disposable type, such as diapers and sanitary pads, have been proposed which are discarded after a single use. Several factors are of importance in determining whether such articles will be acceptable to the consumer. The articles should rapidly receive and dissipate body fluids without a significant amount of backwetting to the wearer's skin and without wicking and leakage from the article, while providing comfort to the wearer. Such absorbent articles also should be available to the consumer at a relatively low cost, since they are not reused.

Much of the cost and deficiencies in prior articles may be attributed to the structure of and the materials used in the articles. In the case of disposable diapers, structures are often provided having an absorbent pad, a fluid impervious backing sheet covering a back surface of the pad, and a fluid pervious top sheet covering a front surface of the pad. Particularly in the case where the absorbent pads are made of a mass of fibers, such as comminuted wood pulp, an absorbent wadding sheet is often placed over the front surface of the pad to maintain structural integrity of the pad when wet. In addition to adding to the cost of the diapers, such top wadding sheets impair the function of the diaper in a number of respects. The wadding sheets impede the rapidity of fluid passage from the top sheet into the pad, and retain fluid adjacent the front surface of the diaper, thus increasing the amount of backwetting from the diaper to the infant. The wadding sheet also adds stiffness to the diaper, thus decreasing the amount of comfort the diaper provides for the infant.

In the past, the top sheet of the diaper, which is usually made of nonwoven material, has been made relatively thick and strong to prevent breaking up of the top sheet when it becomes wet during use. The relatively heavy top sheet utilized in prior diapers also adds significantly to the cost of the diaper. Accordingly, it is desirable to reduce the thickness of the top sheet altogether. Whether or not the top sheet is totally eliminated from the diaper, it is necessary to provide a comfortable surface of the diaper for the infant.

SUMMARY OF THE INVENTION

A principal feature of the present invention is the provision of an absorbent article of simplified construction and reduced cost.

The article of the present invention comprises, an absorbent pad having a front and back surface, a fluid impervious backing sheet covering the back surface of the pad, and a perforated thermoplastic film covering the front surface of the pad. A pattern is fused into the film to enlarge a plurality of perforations in the film and fuse the film to the pad in the locality of the pattern.

A feature of the invention is that the enlarged perforations permit passage of fluid through the film to the pad.

Another feature of the invention is that the film prevents backwetting of fluid from the pad.

Still another feature of the invention is that the fused film maintains the structural integrity of the pad and eliminates the necessity for a top wadding sheet for the pad.

Yet another feature of the invention is that the article permits rapid passage of fluid to the pad due to elimination of the top wadding sheet.

Another feature of the invention is that the article reduces backwetting from the pad due to elimination of the top wadding sheet.

A further feature of the invention is that the article is more pliable and has a better hand due to elimination of the top wadding sheet.

Another feature of the invention is that the pattern defines a discontinuous front surface of the article for placement against the wearer.

Thus, another feature of the invention is that the article provides a comfortable surface for the skin of a wearer.

A feature of this embodiment of the invention is that the conventional top sheet of nonwoven material is eliminated, thus reducing the cost of the article.

In another embodiment of the invention, the article may include a fluid pervious top sheet covering the film. The film is fused to the top sheet in the locality of the pattern to define a discontinuous front surface of the article.

A feature of the invention is that the article provides an improved surface for placement against the wearer and for added comfort.

A further feature of the invention is that the fused film reinforces the top sheet and permits the use of a relatively thin material for the top sheet without breaking up during use.

Thus, a feature of the invention is that elimination of the top wadding sheet and the reduction in thickness of the top sheet reduces the cost of the absorbent article over conventional articles.

In another embodiment of the invention the backing sheet may be fused to the pad in a pattern to define a discontinuous back surface of the article.

Thus, a feature of the invention is that this embodiment of the article has an improved back surface.

Still another feature of the invention is the provision of a method for making the absorbent articles of the present invention.

Further features will become more fully apparent in the following description of the embodiments of this invention and from the appended claims.

DESCRIPTION OF THE DRAWINGS

In the drawings:

FIG. 1 is a diagrammatic view illustrating an apparatus for making an absorbent article according to a method of the present invention;

FIG. 2 is a perspective view of a heating member for the apparatus of FIG. 1;

FIG. 3 is a diagrammatic view illustrating another apparatus for making an absorbent article according to a method of the present invention;

FIG. 4 is a perspective view of a heating member for the apparatus of FIG. 3;

FIG. 5 is a front plan view, partly broken away, illustrating a partially constructed absorbent article or diaper of the present invention;

FIG. 6 is a front plan view, partly broken away, of a disposable diaper of the present invention;

FIG. 7 is a fragmentary sectional view taken substantially as indicated along the line 7—7 of FIG. 6;

FIG. 8 is a perspective view of the diaper of FIG. 6 folded into a box-pleat configuration;

FIG. 9 is a front plan view, partly broken away, illustrating another embodiment of a partially constructed absorbent article or diaper of the present invention;

FIG. 10 is a front plan view, partly broken away, of the disposable diaper of FIG. 9;

FIG. 11 is a fragmentary sectional view taken substantially as indicated along the line 11—11 of FIG. 10; and FIG. 12 is a fragmentary sectional view showing another embodiment of the article of the present invention.

DESCRIPTION OF THE PREFERRED EMBODIMENTS

Although, for convenience, the absorbent article of the present invention will be described as a disposable diaper, it will be understood that the description is applicable to other suitable absorbent articles. For example, other illustrative articles which may be constructed according to the present invention are sanitary pads, maternity napkins, and wound dressings.

Referring now to FIG. 1, there is shown an apparatus, generally designated 20, for making an absorbent article, such as a disposable diaper, according to a method of the present invention. The apparatus 20 has a first section 22 which cuts an absorbent material, such as comminuted wood pulp, into lengths as absorbent pads 24, and places the pads 24 in a spaced relationship on a fluid impervious backing sheet 26, such as polyethylene, as the backing sheet passes onto an endless belt 28. The belt 28 is supported and driven by a pair of rollers 30, with the belt 28 being driven in a direction such that the backing sheet 26 and pads 24 are carried from the first section 22, as indicated by the direction of the arrows in the drawings.

A web of thermoplastic material 32, such as a film of polyethylene, is unwound from a roll 34 and passes beneath a roller 36 to a roller 38 where it joins a web 39 of fluid pervious material, such as a nonwoven material, which is unwound from a roll 40. The webs 32 and 39 pass from the roller 38 to a perforator generally designated 42.

The perforator 42 has an upper roll 44 having a plurality of closely spaced needles or pins 46 projecting outwardly from the roll 44 peripherally around the roll. The perforator 42 also has a lower roll 48 defining a resilient substrate for the upper roll 44 to maintain the webs 32 and 39 against the upper roll and receive the points of the needles 46 as they pass through the webs. The lower roll 48 may have a plurality of metal bristles 50 projecting outwardly from the roll and extending peripherally around the roll, thus defining a brushlike surface for the roll. In another embodiment, the lower roll 48 may have a soft surface, such as rubber, to receive the points of the needles. Thus, as the webs 32 and 39 pass between the upper and lower rolls 44 and 48 of the perforator 42, the needles 46 of the upper roll 44 pass through the webs 32 and 39 and perforate the thermoplastic film or web 32 with perforations, as further described below. The needles 46 of the upper roll 44 may extend throughout a sufficient width of the roll 44, if desired, to perforate the entire width of the web 32.

The perforated webs 32 and 39 then pass over a roller 52 and under a roller 54 to a location over the pads 24 on the belt 28 where the webs are placed over the front surface 56 of the pads, as shown. As shown in FIGS. 1 and 2, a heating member 58 is supported and driven above the placed webs 32 and 39. The heating member 58 has a heated metal roll 61 and a metal network or screen 59 defining a pattern and projecting outwardly from the outer surface of the roll 61. The raised network 59 is heated by the roll 61 and contacts the web 39 of fluid pervious material as the webs 32 and 39 and pads 24 pass beneath the heating member 58, thus heating the thermoplastic film in a network pattern through the web 39. A supporting member 60 is provided beneath the belt 28, such that the pads 24 and webs may be slightly compressed between the heating member 58 and supporting member 60 as the web 32 is heated. The heat applied to the web 32 of thermoplastic material causes a plurality of the perforations in the web to enlarge from the configuration as initially perforated in the locality of the heated pattern. The heated web 32 is also fused to the compressed web 39 and pad 24 in the locality of the pattern, thus defining a discontinuous front surface in the diaper as will be further described below. The heating member 58 has a cutout portion 62 to prevent contact of the heating member 58 against the webs 32 and 39 intermediate the pads 24 as they pass beneath the member 58.

As shown in FIG. 1, a heated element 64, which is mounted for reciprocal vertical movement, has a pair of laterally extending ribs 66 which contact and heat the webs 32 and 39 and the backing sheet 26 along lateral lines intermediate the pads 24, and thus fuse the webs 32 and 39 and backing sheet 26 together adjacent end edges of the pads 24. A supporting member 68 is provided beneath the belt 28 to facilitate operation of the heated element 64 in fusing the webs and backing sheet together. The heated element 64 is spaced away from the webs 32 and 39 when the pads 24 pass beneath the element 64, and is brought into the lower sealing position intermediate end edges of the pads.

Preferably, the webs 32 and 39 and backing sheet 26 have a greater width than the pads 24, such that the webs and sheet extend past side edges of the pads. As the pads pass along the belt 28, the webs and backing sheet covering the pads 24 pass beneath a second heated element 70 having a pair of spaced heated rollers 72 located adjacent the opposed side edges of the pads 24. The heated rollers 72 contact the web 39 and continuously fuse the webs 32 and 39 and backing sheet 26 together along side edges of the pads 24, such that the heat seal lines extend the length of the pads and cross the lateral heat seal lines made by the first heated element 64. A supporting member 74 provides a support surface for operation of the heated rollers 72 in fusing the webs and backing sheet together. The pads 24 then pass from the belt 28 to a second section 76, where the pads are severed from each other intermediate the lateral heat seal lines formed by the heated member 64, and the separated pads are folded and packaged, as desired.

Another apparatus 20 for making absorbent articles according to the present invention is illustrated in FIGS. 3 and 4, in which like reference numerals designate like parts. In this embodiment, the web or webs are heated by a reciprocating heating member 58' which is mounted for vertical movement and which has a heated network or screen 59' on its lower surface. As shown in FIG. 3, the heating member lowers to contact and heat the web 32 while compressing the diaper against the supporting member 60.

As in the apparatus of FIG. 1, the perforator 42 may perforate the web 32 of thermoplastic material prior to placement against the web 39, if utilized. The roll 40 and web 39 of fluid pervious material (shown in dotted lines in FIG. 3) may be omitted from use in the apparatus of both FIGS. 1 and 3, such that only the web 32 of thermoplastic material is placed over the front surface of the pads 24. In this configuration, the heating members 58 and 58' (FIGS. 1 and 3, respectively) fuse a pattern in the web 32 against the front surface 56 of the pads, enlarge perforations in the locality of the heated pattern, and define a discontinuous front surface of the web 32 for the diapers. The heated members 64 and 70, which are described in connection with the apparatus of FIG. 1, may be utilized to fuse the webs 32 and 39 and backing sheet 26 together adjacent side and end edges of the pads 24, if desired.

It will be understood that many other variations are within the scope of the present invention. For example, the perforated web 32 of thermoplastic material may be heated to enlarge the perforations prior to placement of the web 32 against the web 39 of fluid pervious material. If desired, the needles 46 may be spaced from the side edges of the web 32, such that the perforations only overlie the pads or are laterally confined to the areas of the web 32 which are fused to the pads. Also, the needles 46 may be spaced in peripheral portions of the perforator 42, in order that the longitudinal sections of the web 32 intermediate the end edges of the pads are not perforated.

A disposable diaper generally designated 84 which is made according to the present invention with a fluid pervious top sheet is illustrated in FIGS. 5–8. As shown in FIG. 5, the diaper 84 as partially formed has an absorbent pad 24, such as comminuted wood pulp forming a mass of fibers, a fluid impervious backing sheet 26 preferably of a thermoplastic material, such as polyethylene, covering a back surface 29 of the absorbent pad 24, a sheet of cellulose wadding 27 intermediate the backing sheet 26 and pad 24, a film 32 of thermoplastic material, such as polyethylene, having a plurality of small perforations 33 extending through the film, with the film 32 covering a front surface 56 of the pad 24, and a fluid pervious top or cover sheet 39, such as a nonwoven material, covering the film 32. The diaper 84 or pad assembly has a fluid receiving region 41 generally in the longitudinal and lateral central region of the diaper. The perforations 33 in the diaper of FIG. 5 are shown prior to heating, and are shown as extending throughout the width and length of the film 32.

As illustrated in FIGS. 6 and 7, the heated network of the heating member fuses the film 32 to the top sheet 39 and the underlying pad 24 where heated. The heated film 32 thus becomes anchored to fibers in the pad and top sheet in the locality of the pattern, which is facilitated by compression of the diaper in the heated areas. Since fused to areas of the pad, the film 32 maintains structural integrity of the pad when wet, and eliminates necessity for placing a sheet of absorbent wadding over the front surface 56 of the pad, which would otherwise be required to prevent breaking up and balling of the pad during use of the diaper.

Additionally, the heating member forms a pattern 90 of depressed areas 91 and mesh of raised areas 92 in the top sheet 39 and film 32 corresponding to the network on the heating member. The pattern 90 defines a discontinuous front surface to provide added comfort for the infant and improve the appearance of the diaper. At the same time, a large number of perforations 33 in the film 32 are enlarged to openings 33' in the locality of the heated pattern to permit passage of fluid through the film 32.

During use of the diaper fluid passes through the top sheet 39 and the enlarged openings 33' directly into the pad 24. Elimination of the top wadding sheet increases the rapidity with which fluid passes into the pad, since the top wadding sheet normally impedes the passage of fluid into the pad. Additionally, backwetting from the pad to the top sheet is reduced by elimination of the top wadding sheet, since the wadding sheet would normally retain fluid adjacent the top sheet after being wetted. Backwetting from the absorbent pad is also prevented by the film 32 which provides a fluid impervious barrier throughout a substantial area of the diaper. Elimination of the top wadding sheet also permits greater conformability of the diaper, since the top wadding sheet normally causes some stiffness to the front of the diaper, and the diaper of the present invention thus has a better hand and provides a more comfortable surface for the infant's skin. In addition, elimination of the top wadding sheet reduces the cost of materials in the diaper.

Relatively thick nonwoven materials have been utilized in the past for top sheets in diapers to prevent breaking up of the top sheets when wetted or moved during use. However, the thermoplastic film 32, which is fused in areas to the top sheet 39, reinforces the top sheet and permits the use of a relatively thin material for the top sheet in the diaper of the present invention. A normal weight for the nonwoven materials utilized in conventional diapers is approximately 18–22 grams/square yard, whereas a relatively thin top sheet of nonwoven material having a weight of 7–14 grams/square yard may be readily used in the diaper of the present invention without breaking up or tearing of the top sheet during use of the diaper, thus significantly reducing the cost of materials for the diaper. The passage of fibers from the pad through the relatively thin top sheet is prevented by the film 32.

As shown in FIGS. 6 and 7, the top sheet 39, film 32, and backing sheet 26 extend past side and end edges of the pad 24, and the sheets and film are fused on lines 45 along side edges of the pad and lines 47 along end edges of the pad. As shown, the film 32 may be heated only in the central region 41 of the diaper, such that the enlarged openings 33' are spaced from the side and end edges of the pad. Thus, the fluid impervious film 32 and backing sheet 26 provide a fluid barrier adjacent side and end edges of the pad to prevent wicking and leakage from the edges of the pad during use of the diaper. If the perforations 33 extend to the side and end edges of the film 32, the small perforations 33 permit little or no leakage through the film 32. Alternatively, the perforations 33 may be spaced from the side edges of the film 32, as well as the end edges of the film, if desired.

In a preferred embodiment of the diaper of the present invention, the thermoplastic film 32 may have a thickness in the range of 0.2 to 0.5 mils, and the top sheet may have a weight of 10–14 grams/square yard. In a satisfactory structure, the largest distance across the perforations or openings 33 may be in the range of 0.2 to 7 mms prior to heating the film 32, whereas the largest distance across the enlarged openings 33' may be in the range of 0.2 to 8 mms. It is noted in this regard that some of the perforations 33 in the locality of the pattern may not be enlarged when the film 32 is heated.

The film 32, if polyethylene, may be heated at approximately 250° to 300°F. to enlarge the perforations and fuse the film to the top sheet and pad. The size of the openings 33' may be determined in part by the initial size of the perforations 33 and the extent to which the film 32 is heated after being perforated, both in temperature and length of time. It will be understood that the words "perforations" and "perforating", and other words of similar effect, are used herein for convenience, and should not be considered as limiting the present invention. Thus, it is intended that perforations may comprise holes, apertures, slits, or other openings of regular or irregular shape. Also, it is contemplated that perforating comprises an operation or operations which provide such perforations. The enlarged openings 33' may also have a regular or irregular shape.

It will also be apparent that any suitable pattern may be formed in the diaper, as desired. However, in a preferred embodiment the pattern defines a network of depressed areas and a mesh-like configuration of raised areas, as described, with the network being relatively closely spaced to provide a surface of the diaper which is comfortable for the infant and which is aesthetically pleasing. For example, a suitable configuration of the pattern for use on the diaper of the present invention may have a fineness in the range of 4 to 1000 mesh, such as about 144 mesh. If desired, the heating member 58 may have a plurality of closely spaced and heated protuberances or pins depending from its lower surface, in order that a pattern of spaced depressions are defined in the heated diaper.

As illustrated in FIG. 8, the diaper 84 may be folded into a box-pleat configuration along a plurality of longitudinally extending fold lines 51a, 51b, 51a, and 51d defining a longitudinally extending central panel C, a pair of first panels B and D extending from and overlying the front surface of the central panel C, and a pair of outermost panels A and E extending from and overlying the first panels B and D. The pleats in the panels may be retained to the front surface of the central panel C by a pair of adhesive spots 53. The diaper 84 may have a pair of conventional tape fasteners 55 for securing the diaper about an infant during placement. In other respects, the diaper may conform to the structure of the diaper described in connection with FIGS. 6 and 7, and has its patterned front surface facing the infant.

Another embodiment of the present invention is illustrated in FIGS. 9–11, in which like reference numerals designate like parts. In this embodiment, the diaper is constructed without the use of a nonwoven top sheet. As shown in FIG. 9, the partially completed diaper has a plurality of perforations 33 extending through the film 32, as previously described. As illustrated in FIGS. 10 and 11, the pattern 90 in the film 32 defines a discontinuous outer surface of the film and front surface of the diaper. As before, a plurality of the perforations 33 are enlarged to the openings 33' in the locality of the depressed areas 91 in the pattern 90, and the film 32 is fused to the pad 24 in the depressed areas 91 of the film. The pattern 90 formed in the film 32 provides a comfortable surface of the film for contact with the infant's skin, although made of a plastic material. It is apparent that elimination of the top sheet and top wadding sheet in this embodiment of the diaper significantly reduces the cost of the diaper. Any suitable pattern may be used in this embodiment of the diaper, such as the network, as previously described.

Another embodiment of the present invention is illustrated in FIG. 12, in which like reference numerals designate like parts. In this embodiment, a pattern 90' has been fused into the thermoplastic backing sheet 26, such that the depressed areas 91' of the pattern are fused to the back wadding sheet 27 of the pad 24. The pattern 90' defines a discontinuous back surface of the diaper which is aesthetically pleasing and provides a comfortable surface. The pattern may be of any suitable configuration, such as the network defining a mesh of raised areas 92'. It will be apparent that the pattern may be formed in the backing sheet through use of an apparatus and heating member similar to that described in connection with FIGS. 1–4.

The foregoing detailed description is given for clearness of understanding only, and no unnecessary limitations should be understood therefrom, as modifications will be obvious to those skilled in the art.

I claim:

1. An absorbent article, comprising: an absorbent pad having a front surface, a film of thermoplastic material covering at least a portion of the front surface of the pad in a fluid receiving region of the article, a fluid pervious top sheet covering said film in said region, said top sheet having an outer surface facing away from the film, said film having a plurality of fluid transmitting openings extending through the film in said region, and said top sheet being fused against the film in a pattern defining a recessed configuration in the outer surface of the top sheet.

2. The article of claim 1 wherein said film is fused to the pad in the locality of said pattern.

3. The article of claim 1 wherein said pattern defines a mesh-like configuration in said film.

4. The article of claim 3 wherein the fineness of said configuration is in the range of 4 to 1000 mesh.

5. The articles of claim 1 wherein said openings comprise perforations in the film enlarged by heating.

6. The article of claim 5 wherein at least a substantial portion of the enlarged perforations are located in the locality of said pattern.

7. The article of claim 1 wherein said top sheet comprises a nonwoven material having a weight of 7–14 grams/square yard.

8. An absorbent article, comprising: an absorbent pad having a back surface, and a thermoplastic backing sheet covering at least a portion of the back surface of the pad, said backing sheet having an outer surface facing away from the pad and a pattern fused into the sheet against said pad defining a recessed configuration in the outer surface of the backing sheet.

9. A disposable diaper, comprising: an absorbent pad having a front surface, and a perforated film of thermoplastic material covering at least a portion of the front surface of the pad in a fluid receiving region of the diaper, said film having an outer surface facing away from the pad, a closely spaced pattern fused into the film against the pad defining a recessed configuration in the outer surface of the film, and a plurality of fluid transmitting openings in said region, said openings comprising perforations enlarged by heating in the locality of said pattern from a size of 0.2 to 7 mms to a size of 0.2 to 8 mms.

10. A disposable diaper, comprising: an absorbent pad having a front surface, a fluid pervious top sheet covering at least a portion of the front surface of the pad, and a film of thermoplastic material intermediate said top sheet and pad, said film having a pattern fused against the top sheet and pad defining a recessed configuration of the front surface of the diaper, and a plurality of fluid transmitting openings extending through the film in the locality of said pattern, said openings being enlarged from perforations of a smaller size in said film.

11. An absorbent article comprising, an absorbent pad having a front surface, and sheet means, including a perforated film of thermoplastic material, covering at least a portion of the front surface of the pad and having a closely spaced pattern fused into the film to define a recessed configuration of the front surface of the article, said pattern defining a mesh-like configuration in said film, with the fineness of the configuration being in the range of 4 to 1000 mesh, and said film having a plurality of openings comprising a portion of said perforations enlarged from a smaller size by heating in the locality of said pattern.

12. A method of making an absorbent article, comprising the steps of:
    placing a film of thermoplastic material against a back surface of an absorbent pad; and
    fusing a pattern into said film against the back surface of the pad to define a partially recessed outer surface of the film relative the pad.

13. A method of making an absorbent article, comprising the steps of:
    perforating a film of thermoplastic material;
    placing the perforated film and a sheet of fluid pervious material against a surface of an absorbent pad with the film located intermediate the sheet and pad; and
    heating the sheet and film in a pattern to enlarge a plurality of film perforations and fuse the film to the sheet and pad in the locality of the pattern.

14. A method of making an absorbent article, comprising the steps of:
    placing a film of thermoplastic material against a front surface of an absorbent pad;
    placing a sheet of fluid pervious material against an outer surface of the film; and
    fusing a pattern into the film against the sheet and pad to define a partially recessed front surface of the article.

15. The method of claim 14 including the step of perforating said film, and in which said fusing step enlarges a plurality of film perforations in the locality of said pattern.

* * * * *